United States Patent [19]

DeMarco et al.

[11] Patent Number: 5,693,805
[45] Date of Patent: *Dec. 2, 1997

[54] PROCESS TO DERIVATIVES OF PIPERIZINYLCAMPHORSULFONYL OXYTOCIN ANTAGONISTS

[75] Inventors: Anthony M. DeMarco, Glen Gardner; Edward J.J. Grabowski, Westfield; Guo-Jie Ho, Edison; David J. Mathre, Skillman; Khateeta M. Emerson, Hoboken; Richard F. Shuman, Westfield; Paul Sohar, Warren, all of N.J.

[73] Assignee: Merck & Co., Inc., Rahway, N.J.

[*] Notice: The portion of the term of this patent subsequent to May 26, 2012, has been disclaimed.

[21] Appl. No.: 530,098

[22] PCT Filed: Mar. 10, 1994

[86] PCT No.: PCT/US94/02578

§ 371 Date: Sep. 12, 1995

§ 102(e) Date: Sep. 12, 1995

[87] PCT Pub. No.: WO94/20483

PCT Pub. Date: Sep. 15, 1994

Related U.S. Application Data

[63] Continuation-in-part of Ser. No. 30,936, Mar. 12, 1993, abandoned.

[51] Int. Cl.$^6$ .................................................. C07D 295/26
[52] U.S. Cl. ........................................ 544/383; 514/255
[58] Field of Search .................................................. 544/383

[56] References Cited

U.S. PATENT DOCUMENTS

| | | | |
|---|---|---|---|
| 4,347,254 | 8/1982 | Katsube et al. | 514/372 |
| 4,813,998 | 3/1989 | Van Lommen et al. | 504/277 |
| 5,134,123 | 7/1992 | Branca et al. | 546/138 |
| 5,204,349 | 4/1993 | Bock et al. | 544/230 |

FOREIGN PATENT DOCUMENTS

| | | |
|---|---|---|
| 486 280 | 5/1992 | European Pat. Off. |
| A 0 532 097 | 3/1993 | European Pat. Off. |
| A 0 533 240 | 3/1993 | European Pat. Off. |
| A 0 533 241 | 3/1993 | European Pat. Off. |
| A 0 533 242 | 3/1993 | European Pat. Off. |

OTHER PUBLICATIONS

Hirani et al., J. Heterocyclic Chem., 24, p. 489 (1987).

*Primary Examiner*—Emily Bernhardt
*Attorney, Agent, or Firm*—William H. Nicholson; Mary A. Appollina; Melvin Winokur

[57] ABSTRACT

A process for the manufacture of oxytocin receptor antagonists of the following formula (I)

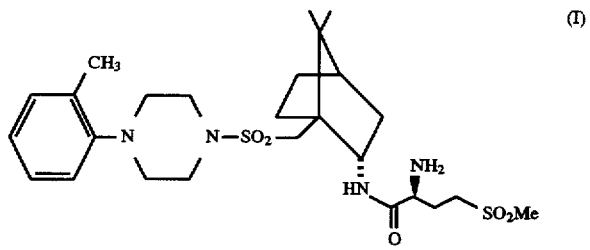

and their crystalline salts is disclosed.

7 Claims, No Drawings

PROCESS TO DERIVATIVES OF PIPERIZINYLCAMPHORSULFONYL OXYTOCIN ANTAGONISTS

This application is a 371 of PCT/US94/02578 filed Mar. 10, 1994 which is a continuation in part of U.S. Ser. No. 08/030,936, filed Mar. 12, 1993 (now abandoned).

FIELD OF THE INVENTION

The present invention provides novel compounds, and methods of their manufacture, such compounds are generally pharmacologically useful as agents in obstetric and gynecologic therapy. The aforementioned pharmacologic activities are useful in the treatment of mammals. More specifically, the compounds of the present invention can be used in the treatment of preterm labor, stopping labor preparatory to Cesarean delivery, and in the treatment of dysmenorrhea. At the present time, there is a need in the area of obstetric and gynecologic therapy for such agents.

BACKGROUND OF THE INVENTION

In the field of obstetrics, one of the most important problems is the management of preterm labor. A significant number of the pregnancies progressing past 20 weeks of gestation experience premature labor and delivery, which is a leading cause of neonatal morbidity and mortality. Despite major advances in neonatal care, retention of the fetus in utero is preferred in most instances.

Tocolytic (uterine-relaxing) agents that are currently in use include $\beta_2$-adrenergic agonists, magnesium sulfate and ethanol. Ritodrine, the leading $\beta_2$-adrenergic agonists, causes a number of cardiovascular and metabolic side effects in the mother, including tachycardia, increased renin secretion, hyperglycemia (and reactive hypoglycemia in the infant). Other $\beta_2$-adrenergic agonists, including terbutaline and albuterol have side effects similar to those of ritodrine. Magnesium sulfate at plasma concentrations above the therapeutic range of 4 to 8 mg/dL can cause inhibition of cardiac conduction and neuromuscular transmission, respiratory depression and cardiac arrest, thus making this agent unsuitable when renal function is impaired. Ethanol is as effective as ritodrine in preventing premature labor, but it does not produce a corresponding reduction in the incidence of fetal respiratory distress that administration of ritodrine does.

It has been proposed that a selective oxytocin antagonist would be the ideal tocolytic agent. In the last few years, evidence has accumulated to strongly suggest that the hormone oxytocin is the physiological initiator of labor in several mammalian species including humans. Oxytocin is believed to exert this effect in part by directly contracting the uterine myometrium and in part by enhancing the synthesis and release of contractile prostaglandins from the uterine endometrium/decidua. These prostaglandins may, in addition, be important in the cervical ripening process. By these mechanisms, the process of labor (term and preterm) is initiated by a heightened sensitivity of the uterus to oxytocin, resulting in part as a result of a well-documented increase in the number of oxytocin receptors in this tissue. This "up-regulation" of oxytocin receptors and enhanced uterine sensitivity appears to be due to trophic effects of rising plasma levels of estrogen towards term. By blocking oxytocin, one would block both the direct (contractile) and indirect (enhanced prostaglandin synthesis) effects of oxytocin on the uterus. A selective oxytocin blocker, or antagonist, would likely be more efficacious for treating preterm labor than current regimens. In addition, since oxytocin at term has major effects only on the uterus, such an oxytocin antagonizing compound would be expected to have few, if any, side effects.

The compounds made by the process of of the present invention can also be useful in the treatment of dysmenorrhea. This condition is characterized by cyclic pain associated with menses during ovulatory cycles. The pain is thought to result from uterine contractions and ischemia, probably mediated by the effect of prostaglandins produced in the secretory endometrium. By blocking both the direct and indirect effects of oxytocin on the uterus, a selective oxytocin antagonist can be more efficacious for treating dysmenorrhea then current regimens. An additional use for the present invention is for the stoppage of labor preparatory to Cesarean delivery.

It is, therefore, a purpose of this invention to provide a process for the manufacture of substances which more effectively antagonize the function of oxytocin in disease states in animals, preferably mammals, especially in humans. It is another purpose of this invention to prepare novel compounds which more selectively inhibit oxytocin. It is still another purpose of this invention to provide a method of antagonizing the functions of oxytocin in disease states in mammals. It is also a purpose of this invention to develop a method of preventing or treating oxytocin-related disorders of preterm labor and dysmenorrhea by antagonizing oxytocin.

It has now been found that compounds of formula I are antagonists of oxytocin and bind to the oxytocin receptor. When the oxytocin receptor is bound by the compounds of the present invention, oxytocin is antagonized by being blocked from its receptor and thus being unable to exert its biologic or pharmacologic effects. These compounds are useful in the treatment and prevention of oxytocin-related disorders of animals, preferably mammals and especially humans. These disorders are primarily preterm labor and dysmenorrhea. The compounds would also find usefulness for stoppage of labor preparatory to Cesarean delivery.

SUMMARY OF THE INVENTION

The instant invention involves a process for the manufacture of a pharmaceutically acceptable salt of a free base compound of the formula

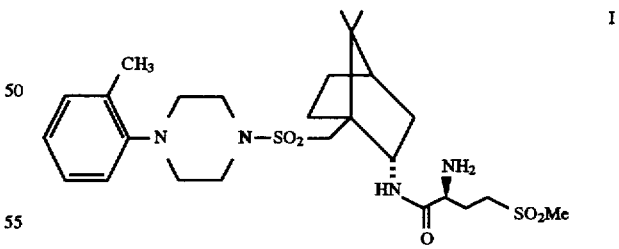

I comprising the steps of
(a) reacting the compounds of the formulas

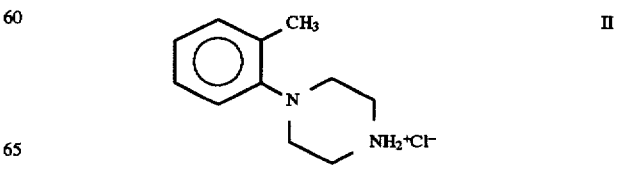

II

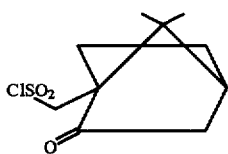

so as to form the ketone of the formula

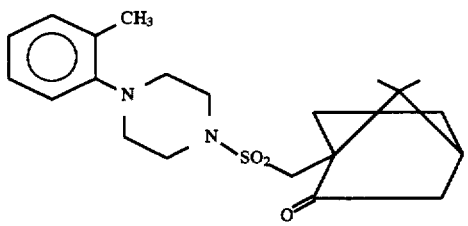
III (b) reacting the product of step (a) with hydroxylamine to form the corresponding oxime of the formula

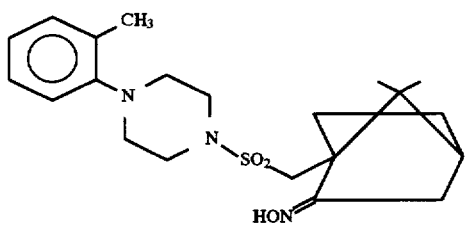
IV (c) reducing the product of step (b) in the presence of Raney nickel, methanol and a suitable alkali metal hydroxide, alkaline earth hydroxide or ammonium hydroxide to form the endo (VI) and exo (VII) amine products

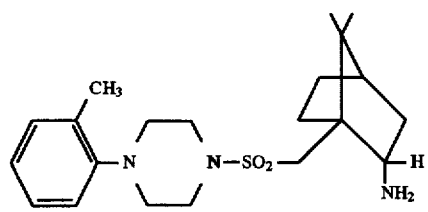
VI and

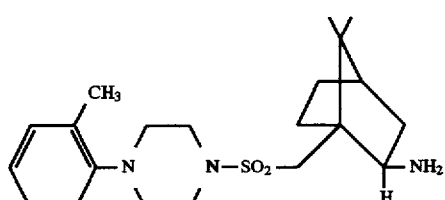
VII (d) selectively reacting the endo amine product of step (c) with a compound of the formula

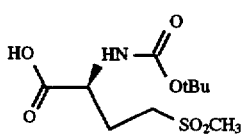
VIII to give the product of the formula

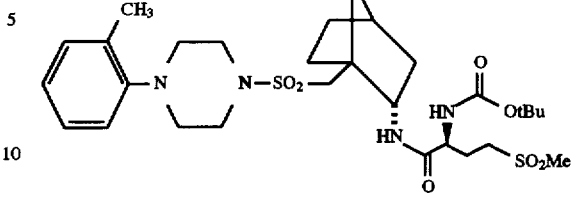
IX (e) deprotecting the product of step (d) to give the free base product of formula

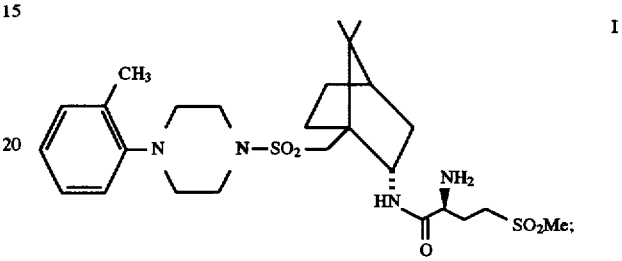
I and (f) reacting the deprotected free base product of step (e) with a selected acid to give the corresponding acid salt.

In one embodiment of the invention is the process wherein said acid is selected from the group consisting of sulfuric acid, hydrochloric acid, phosphoric acid, acetic acid, maleic acid and tartaric acid.

In one class of the embodiment is the process wherein said acid is sulfuric acid.

In one subclass is the process whereby said endo and exo amine products of step (c) are separated by selective pH extraction.

In a second subclass is the process whereby said endo and exo amine products of step (c) are separated by HPLC in the presence of a buffer in the range of pH 5 to pH 7.

Illustrative of this second subclass is the process where said buffer is at pH 6.

In a third subclass of the invention is the process wherein said endo selective reaction is carded out in the presence of a suitable acyl activating transfer catalyst.

Illustrative of this third subclass is the process wherein said acyl activating transfer catalyst is hydroxybenzotriazole hydrate.

A further illustration of this subclass is the process which is carried out in the presence or a suitable diimide.

Exemplifying this subclass is the process where said diimide is ethyl-3-(3-dimethylamino) propyl carbodiimide hydrochloride.

More specifically exemplifying the invention is a process for the manufacture of a sulfate salt product compound of the formula

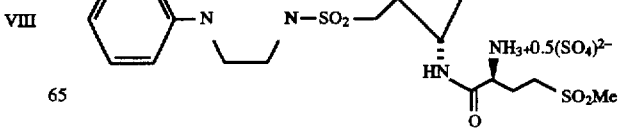
X comprising the steps of (a) reducing an oxime of the formula

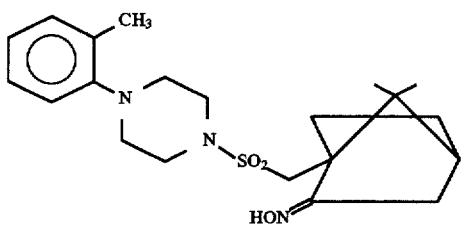

in the presence of Raney nickel, methanol and a suitable alkali metal hydroxide, alkaline earth hydroxide or ammonium hydroxide to produce an endo amine compound of the formula

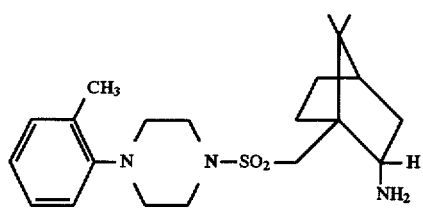

(b) reacting the endo amine product of step (a) with a compound of the formula

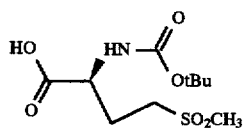

to produce a protected amine compound of the formula

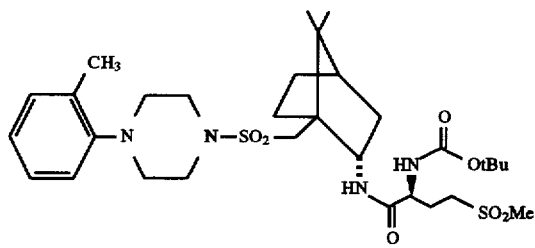

(c) deprotecting the product of step (b) to produce a compound of the formula

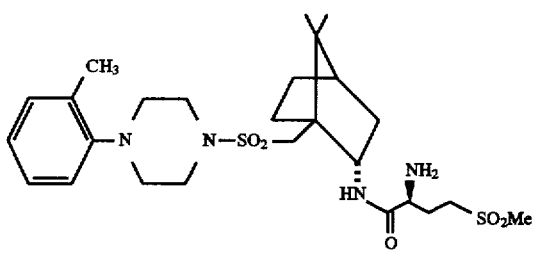

(d) reacting the product of step (c) with sulfuric acid to produce the sulfate salt product X.

Illustrative of the invention is the process comprising; the additional step of reacting a ketone of the formula

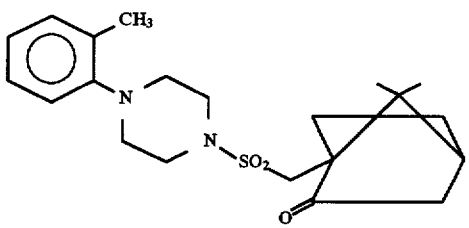

to produce the ox/me starting compound of step (a).

Further illustrating the invention is the process comprising the additional step of reacting o-tolyl piperazine with (+)-10-camphorsulfonyl chloride to produce the ketone.

Exemplifying the invention is the process in which said alkali metal hydroxide is sodium hydroxide.

A more specific illustration of the invention is a process for making a crystalline pharmaceutically acceptable salt of a free base compound I of the formula

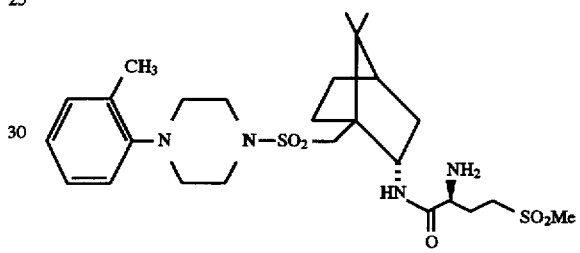

comprising the step of reacting the free base compound with a selected acid to give the corresponding acid salt in crystalline form.

Further exemplifying the invention is the process wherein said acid is sulfuric acid.

Another example of the invention is a crystalline pharmaceutically acceptable salt of a compound I of the formula

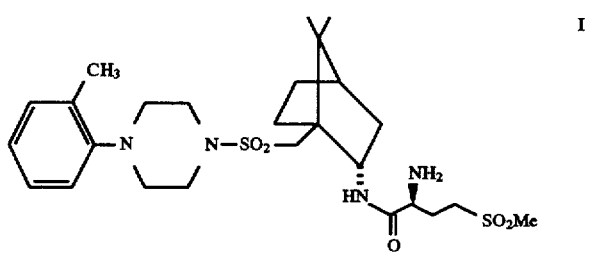

made by this process.

Further illustrating the invention is the compound wherein said crystalline salt is selected from the group consisting of sulfate, tartrate, maleate, hydrochloride, acetate and phosphate salts.

Also included within the scope of the invention is a crystalline pharmaceutically acceptable salt of a compound I of the formula

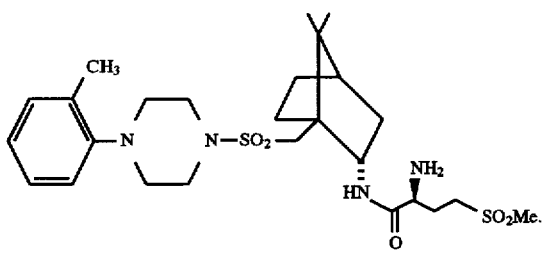

In a second embodiment is the compound wherein said crystalline salt is selected from the group consisting of sulfate, tartrate, maleate, hydrochloride, acetate and phosphate salts:

In one class of this embodiment is a crystalline pharmaceutically acceptable sulfate salt of a compound I of the formula

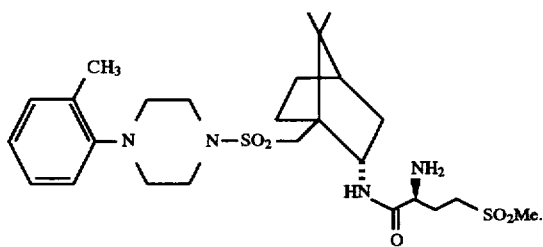

Also included in the invention is a crystalline compound IX of the formula

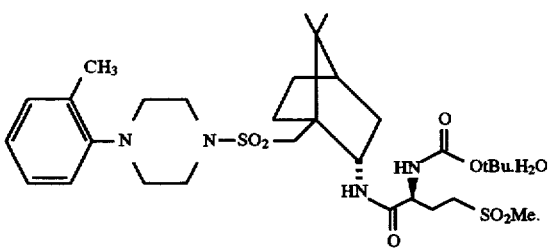

Compound X is prepared in 60–65% overall yield from commercially available 1-(2-tolyl)piperazine, (+)-10-camphorsulfonyl chloride, and N-BOC-(S)-methionine sulfone.

EXAMPLE 1

Schotten-Bauman Procedure

To a mechanically stirred suspension of 1-(2-tolyl) piperazine hydrochloride II (5.00 kg, 23.5 mol) in toluene (25.0 L) was added 5.0M aqueous sodium hydroxide (11.8 L, 59.1 mol). The mixture was stirred for 0.5 h at 20°–25° C. until all of the solid dissolved. The two-phase mixture was cooled to 0°–5° C. A solution of (+)-10-camphorsulfonyl chloride III (7.71 kg, 30.8 mol) in dry toluene (14.0 L) was then added to the rapidly stirred mixture over a 1 h period. During the addition, the reaction temperature was maintained at 0°–5° C. The reaction mixture was stirred for an additional 0.5 h at 0°–10° C., then assayed for completion by HPLC.

| Assay Procedure: | An aliquot (20 µL) of the upper (toluene) layer is diluted to 10.0 mL with 50:50 H₂O/MeCN and then analyzed by HPLC. |
|---|---|
| Instrument: | HP 1090M |
| Column: | 4.6 × 250 mm Inertsil ODS(2) [MetaChem Inc.] |
| Eluent A: | H₂O (0.02M phosphate adjusted to pH 6.0) |
| Eluent B: | MeCN |
| Linear Gradient: | 70:30 to 20:80 A:B over 25 minutes |
| Flow Rate: | 1.5 µL/min. |
| Temperature: | 45° C. |
| Injection: | 10.0 µL |
| Detection: | UV 210 nm |
| Retention Times: | 1-(2-tolyl)piperazine II  3.03 min. |
| | toluene  15.3 min. |
| Ketone Product IV | 20.9 min. |

The reaction was considered complete when less than 1% of 1-(2-tolyl)piperazine II (vs the ketone product IV) remained. If necessary, additional camphorsulfonyl chloride III (and aqueous sodium hydroxide depending on the pH of the aqueous layer) can be added.

After the reaction was complete the mixture was warmed to 20°–25° C., and the layers partitioned. The upper (toluene) layer was sequentially washed with 1M aqueous sodium bicarbonate (2×6.4 L) and water (2×6.4 L). The toluene solution was filtered through a medium-porosity sintered glass funnel and then concentrated in vacuo (1000 to 10 mBar, 45° C.) to a volume of ca. 13 L. Heptane (38.5 L) was added slowly while maintaining the temperature at 45° C. The mixture was cooled to 20°–25° C, aged for 15 h at this temperature, filtered, and the cake washed with 9:1 (v/v) heptane/toluene (2×2.5 L) and heptane (2×2.5 L). The product was air-dried, and then dried in vacuo (100 mBar, nitrogen sweep, 45° C.) to constant weight to give ketone IV as an off-white crystalline solid.

mp: 124°–127° C.

HPLC: >99 area % (above method)

¹HNMR: consistent

Specific Rotation: [a]589=+22.8° (c=1.02 MeOH)

EXAMPLE 2

Sodium Acetate Procedure

A mechanically stirred suspension of ketone IV (4.40 kg, 11.3 mol), hydroxylmine hydrochloride (1.18 kg, 16.9 mol) and sodium acetate (1.20 kg, 14.7 mol) in ethanol (22 L) was heated for 34 h at reflux to give the corresponding oxime product. The ketone IV was not completely soluble at room temperature, but dissolved upon warming the mixture to reflux. The sodium acetate reacted with the hydroxylamine hydrochloride to give hydroxylamine, acetic acid, and sodium chloride. The sodium chloride formed a precipitate which remained out of solution during the course of the reaction. The progress of the reaction can be followed by HPLC.

| Assay Procedure: | An aliquot (100 µL) is diluted to 25.0 mL with 50:50 H₂O/MeCN and then analyzed by the previously described HPLC method. |
|---|---|
| Retention Times: | (oxime V)  19.2 min. |
| | (ketone IV)  20.9 min. |

The reaction was considered complete when less than 1% of the ketone IV remained unreacted. After the reaction was complete, the mixture was cooled to 60°–65° C. At this point water (44 L) was added over a 0.5 h period. During the addition, the sodium chloride dissolved and the product began to crystallize. The mixture was stirred for 14 h at 20°–25° C., cooled to 10° C., and then stirred at this temperature for 4 h. The mixture was filtered and the cake washed with water (3×4.0 L). The resultant product was air-dried, and then dried in vacuo (100 mBar, nitrogen sweep, 45° C.) to constant weight to give the oxime V as a white, crystalline solid.

mp: 170°–172° C.

HPLC: 99 Area % (Above Method)

Specific Rotation: [a]589=−8.17° (c=1.0 MeOH)

$^1$H NMR: consistent

EXAMPLE 3

Preparation of Corresponding Endo Amine VI by 2-Methoxyethanol Procedure

A solution of the oxime product V of Example 2 (650 g, 1.60 mol) and 5.0M aqueous sodium hydroxide (325 mL, 1.63 mol) in 2-methoxyethanol (12.0 L) was pumped into a 5-gal stainless steel autoclave. The autoclave was then charged with a slurry of Raney nickel (325 g) in 2-methoxyethanol (3.0 L), followed by a rinse of 2-methoxyethanol (1.0 L). The batch was run in two 650 g portions and then combined during the work-up. The total amount of 2-methoxyethanol used should be 20 mL/g of oxime V. More concentrated solutions result in a lower endo/exo ratio. The vessel was purged with nitrogen, and then pressurized to 3 atm (44 psi) with hydrogen (The vessel must be purged with nitrogen prior to the introduction of hydrogen). The reaction mixture was then agitated for 24 h at 25°–27° C. The progress of the reaction can be followed by hydrogen uptake and/or HPLC. For the HPLC assay an aliquot (500 µL) is diluted to 25.0 mL with 50:50 (v/v) H$_2$O (0.02M KH$_2$PO$_4$)/MeCN then analyzed by the previously described method.

| Retention Times: | Endo amine VI | 12.0 min. |
|---|---|---|
| | Exo amine VII | 17.1 min. |
| | Oxime V | 19.2 min. |

The reaction was considered complete when less then 1% of oxime or the intermediate hydroxyamine remains. The endo/exo ratio for this reaction was 87:13. We found that, when using 2-methoxyethanol as the reaction solvent, reaction temperature has a decided effect on the endo/exo ratio. In an earlier run (same scale) the reaction temperature approached 30° C., and we obtained an 85:15 endo/exo ratio. The batch was transferred out of the autoclave, and the autoclave then rinsed with toluene (10–12 L). The batch and rinses were then filtered through a 30 cm diameter polypropylene filter pot containing a 2.5 cm bed of "Dicalcite®" (previously washed with 2-methoxyethanol and toluene). The cake was then washed with toluene (4×1.0 L) (Caution: Raney nickel is easily ignited when dry. Great care must be taken during this filtration and subsequent handling. The catalyst must never be sucked dry in the presence of oxygen (air), but should always be covered with the solvent in use, and finally thoroughly washed from the cake. A nitrogen filled plastic bag was used to cover the filter pot during this operation.) The filtrate and cake washes were combined with a previous batch (same size run, endo/exo ratio 85:15). The solution was then concentrated in vacuo (pressure, temperature) using a 20-L Buchi evaporator, and then flushed with toluene (5×3 L) to displace most of the 2-methoxyethanol. Toluene forms an azeotrope containing 25 wt % 2-methoxyethanol at 1 atm (bp 106° C.).

The batch was ultimately concentrated to a thick slurry (ca. 4–6 L). This was then redissolved in toluene (10 L) and the solution transferred into a 35-L extractor. The mixture was then washed with water (1×6 L; 4×4 L) to remove the sodium hydroxide, and any residual 2-methoxyethanol. HPLC analysis of the aqueous layers showed very little product. The toluene solution was concentrated in vacuo (high-vac, 40°–45° C.) to a slurry (ca. 3 L), and then flushed with toluene (3×2 L) to remove residual water. The batch was ultimately concentrated in vacuo to a thick slurry (ca. 3 L), cooled to 20°–25° C., and the mixture then diluted with hexane (8 L). The mixture was aged for 18 h at 5°–10° C. and then filtered. The cake was washed with hexane (4×1 L). The product was air-dried, then dried in vacuo (100 mBar, 40° C.) to constant weight to give the amine as a white crystalline solid.

mp: 145°–147° C.

HPLC: 85.7:14.3 endo/exo ratio $^1$N NMR: consistent

EXAMPLE 4

Raney Nickel in Methanol Procedure

A suspension of oxime V (900 g, 2.22 mol), 5.0N aqueous sodium hydroxide (0.445 L, 2.22 mol), and Raney nickel (500 g) in methanol (12 L) was pumped into a 20-L Hastelloy autoclave, followed by a rinse of methanol (1.5 L). The vessel was purged with nitrogen, and then pressurized to 3 atm (44 psi) with hydrogen. (Caution: the vessel must be purged with nitrogen prior to the introduction of hydrogen.) The reaction mixture was vigorously agitated at 25°–30° C. while monitoring the progress of the reaction by hydrogen uptake and/or HPLC.

| Assay Procedure: | An aliquot (500 µL) is diluted to 25.0 mL with 50:50 (v/v) H$_2$O (0.02M KH$_2$PO$_4$)/MeCN and then analyzed by the previously described HPLC method. | |
|---|---|---|
| Retention Times: | Endo amine VI | 12.0 min. |
| | Exo amine VII | 17.1 min. |
| | Oxime V | 19.2 min. |

After 16 h, the reaction was found to be 95% complete (5% unreacted oxime V) with an endo/exo ratio of 87:13. The vessel was charged with additional Raney nickel (200 g), and the mixture vigorously agitated for 6 h at 25°–30° C. At this point the reaction was considered to be complete (<0.3% untreated oxime V) with an endo/exo ratio of 87:13. The batch was transferred out of the autoclave, and the autoclave rinsed with methanol (4 L). The mixture was filtered through a medium frit sintered-glass funnel containing a small bed of "Celite®" (ca. 1 in, previously washed with 0.1M sodium hydroxide in methanol). The catalyst cake was washed with the autoclave rinse (divided into three portions) and finally with fresh methanol (2.5 L). [Caution: Raney nickel is easily ignited when dry. Great care must be taken during this filtration and subsequent handling. The catalyst must never be sucked dry in the presence of oxygen (air) and should always be covered with the solvent in use, and finally with water after all of the product has been washed from the catalyst cake. A nitrogen filled plastic bag was used to cover the filter pot during this operation.] The filtrate and cake washes were combined and then concentrated in vacuo (1000 to 100 mBar, 20°–30° C.) to a volume of 4 L. During the concentration the product began to crystallize to give a thick (but stirrable) slurry. The mixture was diluted with water (16 L), and the concentration continued to a volume of 16 L. The mixture was then stirred for 24 h at 20°–25° C., was filtered, and the product washed with water (4×1 L; until the pH of the wash was neutral). The product was air-dried, and then dried in vacuo (100 mBar, 40°, nitrogen sweep) to constant weight to afford the amine product as a white crystalline solid.

mp: 145°–147° C.
HPLC: 87:13 endo/exo ratio (Above Method)
$^1$H NMR: consistent

EXAMPLE 5

Separation of Endo and Exo Amine Isomers by Selective PH Extraction

To a well stirred, two-phase mixture containing the amines VI+VII (16.6 g, 78:22 endo/exo), water (200 mL), and toluene (275 mL) was added phosphoric acid (85%) portionwise until the pH of the aqueous layer was 4.9±0.1. The mixture was allowed to settle, and the layers separated. The two layers were analyzed by HPLC (above method). The majority of the exo amine VII (3.2 g) remained in the toluene layer, and was discarded. The aqueous layer, containing the the desired endo amine VI, was adjusted to pH 7.5±0.5 with 5.0M aqueous sodium hydroxide, and was then extracted with toluene (250 mL). The toluene layer was washed once with water (50 mL) and was then concentrated in vacuo to constant weight.

HPLC: 96:4 endo/exo (above HPLC method)

EXAMPLE 6

Endo Selective Coupling Reaction

In a 100-L reaction vessel fitted with a mechanical stirrer, teflon-coated cooling coils, teflon-coated thermocouple probe, and nitrogen inlet containing a solution of the amine VI+VII (3.60 kg total; 7:13 endo/exo; 3.13 kg, 8.00 mol endo) in isopropyl acetate (53 L) were sequentially added water (21 L), N-BOC-(S)-methionine sulfone VIII (2.36 kg, 8.40 mol), and hydroxybenzotriazole hydrate (HOBT, 61 g, 0.40 mol). The mixture was stirred at 20°–25° C. until all solids dissolved, and was then cooled to 0°–2° C. To the rapidly agitated mixture was added ethyl-3-(3-dimethylamino)propyl carbodiimide hydrochloride (EDC, 1.69 kg, 8.80 mol) portionwise over a 0.5 h period, while maintaining the internal temperature at 0°–2° C. The mixture became two clear phases after the addition of EDC. The mixture was stirred for 18 h at 0°–2° C. The progress of the reaction can be followed by HPLC.

| Assay Procedure: | An aliquot (250 μL) is diluted to 50.0 mL with 50:50 (v/v) H$_2$O (0.02M KH$_2$PO$_4$)/MeCn and then analyzed by the previously described HPLC method. | |
|---|---|---|
| Retention Times: | N-BOC-(S)-methicone sulfone | 1.9 min. |
| | HOBT | 2.6/2.8 min. |
| | Endo Amine VI | 12.0 min. |
| | Exo Amine VII | 17.1 min. |
| | Exo isomer of N-BOC-Protected Amine IX | 20.5 min. |
| | Endo isomer of N-BOC-Protected Amine IX | 21.4 min. |

The reaction was considered complete when the amount of endo amine VI remaining unreacted was <2%, with the endo/exo ratio of the product 98:2. Increasing the mount of EDC or N-BOC-(S)-methionine Sulfone VIII used resulted in more of the exo amine VII reacting, thereby decreasing the selectivity of the coupling reaction. After the reaction was complete, 2N aqueous hydrochloric acid (7.0 L) was added, and the mixture was warmed up to 16° C. and stirred for 15 min at 20° C. The mixture was allowed to settle, and the bottom (aqueous) layer was removed. The upper (product) layer was sequentially washed with water (10 L), 1M aqueous sodium bicarbonate (10 L), and finally water (10 L). The solution was then concentrated in vacuo (1000 to 100 mBar, 35°–40° C.) to a volume of 10 L. The solution was diluted with n-propanol (30 L) and was then concentrated in vacuo (100 mBar, 40°–45° C.) to a volume of 10 L to remove the remaining isopropyl acetate. The solution was diluted with n-propanol to a volume of 21 L, heated to 45°–50° C., and then diluted with water (10.5 L). The product was then crystallized by allowing the mixture to slowly cool to 20° C. (seeding if necessary). The mixture was stirred for 48 h at 20°–22° C., was filtered, and the cake washed with 60:40 (v/v) n-propanol/water (2×5 L). The product was air-dried to constant weight to afford crystalline IX as the monohydrate (i.e., a whim crystalline solid). Crystallization of the N-BOC Protected Amine IX increased the purity by reducing the mount of the exo coupled by-product from ca. 2% to <0.2%. Upon further drying of IX in vacuo (10 mBar, 45° C.), the crystalline material lost water and became an amorphous solid.

Yield: 4.72 kg (90% yield) of N-BOC Protected Amine IX as a white amorphous solid.

mp: 101°–103° C.
HPLC: >99.9% endo/exo (above HPLC method)
$^1$H NMR: consistent
Specific Rotation: [a]589=+3.1° (c 1.0, MeOH)

EXAMPLE 7

Preparation of Crude Free Base I Via Trifluoroacetic Acid Deprotection Procedure To a mechanically stirred solution of N-BOC protected amine IX (90 g, 140 mmol) in toluene (900 mL) at 20° C. was added trifluoroacetic acid (TFA, 160 g, 1.40 mol) portionwise over a 0.5 h period. During the initial stages of the addition the internal temperature rose to ca. 30° C. The amount of trifluoroacetic acid should not be reduced. The use of smaller amounts of trifluoroacetic acid resulted in the formation of the crystalline trifluoroacetic acid salt of N-BOC protected amine IX, which was not deprotected under these reaction conditions. The mixture was stirred for 18–24 h at 20°–25° C. During the course of the reaction, a second liquid phase (containing the trifluoroacetic acid salt of amine I) was formed. The progress of the reaction can be monitored by HPLC.

| Assay Procedure: | An aliquot (250 μL) of the toluene layer is diluted with ethanol (5 mL), is concentrated in vacuo (to remove the majority of the toluene), the residue is diluted to 50.0 mL with (50:50 (v/v) H$_2$O (0.02M KH$_2$PO$_4$)/MeCN, and is then analyzed by the previously described HPLC method. In addition, an aliquot (25 μL) of the TFA layer, is worked-up and analyzed by the same procedure. | |
|---|---|---|
| Retention Times: | Amine I | 14.8 min. |
| | Toluene | 15.3 min. |
| | exo Isomer of N-BOC-Protected Amine IX | 20.5 min. |
| | endo Isomer of N-BOC-Protected Amine IX | 21.4 min. |

The reaction was considered complete when the amount of N-BOC Protected Amine IX remaining was <2%. After the reaction was complete, the mixture was cooled to 5° C. To the well stirred mixture was then added water (620 mL), while maintaining the internal temperature <10° C. The vessel was fitted with a pH probe. To the well stirred mixture was then added 5M aqueous sodium hydroxide (282 mL, 1.41 mol) portionwise while monitoring the pH of the aqueous phase. The internal temperature rose to 20°–25° C. during the addition. The pH rose to 12 by the end of the addition. After the neutralization was complete, agitation was stopped, and the mixture was partitioned. The upper (toluene) layer was washed with water (2×90 mL) to remove residual sodium hydroxide and/or sodium trifluoroacetate. The toluene layer was then extracted with 1M aqueous hydrochloric acid (2×700 mL). The two aqueous extracts were combined and then washed with toluene (1×700 mL) to remove any residual N-BOC Protected Amine IX. The aqueous layer, containing the amine I, was adjusted to pH 10 with 5M aqueous sodium hydroxide (282 mL, 1.41 mol) and the product then extracted into toluene (800 mL). The toluene layer was washed with water (2×80 mL) to remove residual sodium hydroxide and/or sodium chloride. The toluene layer was then concentrated in vacuo (1000 to 100 mBar, 40°–45° C.) to a syrup, and was then flushed with methanol (3×250 mL) to displace the residual toluene. The residue was then dissolved in methanol, bringing the volume to 700 mL. This solution containing the crude amine I as the free base was carried on "as is" to the next step (i.e., the salt formation of Examples 9–15).

HPLC: 99.8:0.2 endo/exo

EXAMPLE 8

Preparation of Crude Free Base I Via Sulfuric Acid Deprotection Procedure

To a mechanically stirred solution of 1M aqueous sulfuric acid (1.0 L) at 40° C. was added the N-BOC protected amine IX (100 g, 0.153 mol) portionwise over a 45 rain period. The resulting suspension was stirred at 40° C. until the reaction was judged to be complete by HPLC (ca. 4 h, the suspension became a homogenous solution during the reaction). After the reaction was complete, the solution was cooled to 10°–15° C., and washed with isopropyl acetate (250 mL) to remove any unreacted N-BOC protected amine IX. Isopropyl acetate (800 mL) was added, and the two-phase mixture neutralized with 5M aqueous sodium hydroxide (ca. 400 mL, 2 mol; to pH 9–10) while the temperature was maintained at ca. 20° C. The layers were separated, and the isopropyl acetate layer washed with water (2×200 mL) to remove any residual salts. The isopropyl acetate layer was concentrated in vacuo (40° C., 150–200 mBar) to a volume of ca. 300 mL. n-Propanol (500 mL) was added, and the mixture again concentrated in vacuo (40° C., 150°–200 mBar) to a volume of ca. 300 mL to remove the remaining isopropyl acetate. n-Propanol was then added to bring the volume of the solution to 800 mL. The solution was filtered through a medium-porosity sintered glass funnel, and then used "as is" in the next step (i.e., the salt formation of Examples 9–15).

EXAMPLE 9

Preparation of the Crystalline Sulfate Salt X in Methanol

A clean, dust-free 2 L round-bottomed flask was fitted with a mechanical stirrer, teflon-coated thermocouple probe, and nitrogen inlet. The methanol solution (700 mL) of crude amine I free base of Example 7 (HPLC assay: 73.8 g, 0.133 mol) was transferred into the flask through a 10 μm sintered-glass filter, followed by a methanol rinse (70 mL). To the well stirred mixture at 20°–22° C. was then added 1.0 M sulfuric acid in methanol (66.5 mL, 66.5 mmol) over a 15 min period. [Caution: concentrated sulfuric acid (97%, 6.72 g, 66.5 mmol) should be added to pre-cooled (−20° C.) methanol (60 mL).] No exotherm was observed during the addition of the methanolic sulfuric acid to the batch. After the addition was complete the batch was seeded (1 g). Very shortly after the addition of the seed, the product began to crystallize. At this point it was necessary to speed up the stirrer to break up the mass. The mixture stirred for 18–24 h at 20°–22° C. The mixture was filtered, and the cake sequentially washed with methanol (3×70 mL) and acetone (3×70 mL). The product was air-dried (2 h), then dried in vacuo (100 mBar, nitrogen sweep, 45° C.) to constant weight. Prior to packaging, the batch was sieved through a #20 mesh screen.

Yield: 76.3 g (95% yield) of Amine I Sulfate Salt X as a free-flowing white crystalline solid.

HPLC: >99.8 Area % (Above Method)

¹HNMR: consistent

K.F. 0.4%

Titration (NaOH): 101.0%

Microscopy: anisotropic needle like

Specific rotation: [a]405+58.7° (c 2.0, 50:50 H₂O (PO₄ buffer)/MeCN

EXAMPLE 10

Preparation of the Crystalline Sulfate Salt X in n-Propanol

A 2-L three-necked flask fitted with a mechanical stirrer, a Teflon-coated thermocouple probe, and a nitrogen inlet tube was charged with the filtered solution of crude amine I free base in n-propanol of Example 8 (800 mL; containing 81.9 g, 0.148 mol of the free base by HPLC and/or titration). To this solution was slowly added dilute (ca. 1M) aqueous sulfuric acid (0.986M, 75.0 mL, 0.074 mol) over a 0.5 h period at ca. 20° C. (seeding if necessary). The mixture was aged for 16 h at 20° C., then filtered. The cake was washed with 9:1 (v/v) n-propanol/water (100 mL), followed by acetone (2×125 mL). The product was air dried, and then dried in vacuo (55° C., N2 sweep) to constant weight.

Yield: 86.8 g (97%) of Amine I Sulfate Salt X as a whim crystalline solid.

HPLC: no new impurities >0.05% detected

GC: residual solvents (isopropyl acetate, n-propanol, t-butanol, and acetone) all <0.01%.

¹H NMR: consistent

EXAMPLE 11

Preparation of the Crystalline Hydrochloride Salt of Amine I

To a mechanically stirred solution of crude amine I free base (5.55 g, 10.0 mmol) in ethanol (50 mL) was added 1M ethanolic hydrochloric acid (10 mL, 10 mmol) and water (200 mg). The mixture was seeded (100 mg), and the product allowed to crystallize. The mixture was stirred for 18–24 h at 20°–22° C., filtered, and the cake washed with ethanol (2×5 mL) and acetone (2×5 mL). The product was air-dried (2 h), then dried in vacuo (100 mBar, nitrogen sweep, 35° C.) to constant weight.

Yield: 5.48 g (90%) of amine I hydrochloride salt (monohydrate) as a white crystalline solid.

HPLC: >99.8 area% (above method)

¹H NMR: consistent

K.F. 3.1% titration (AgNO₃) 5.9% microscopy: anisotropic needle-like

EXAMPLE 12

Preparation of the Crystalline Phosphate Salt of Amine I

To a mechanically stirred solution of crude amine I free base (5.55 g, 10.0 mmol) in ethanol (50 mL) was added 1M ethanolic phosphoric acid (10 mL, 10 mmol). The mixture was seeded (100 mg), and the product allowed to crystallize. The mixture was stirred for 18–24 h at 20°–22° C., filtered, and the cake washed with ethanol (2×5 mL) and acetone (2×5 mL). The product was air-dried (2 h), then dried in vacuo (100 mBar, nitrogen sweep, 35° C.) to constant weight.

Yield: 5.77 g (85%) of amine I phosphate salt (1.5 hydrate) as a white crystalline solid.

HPLC: >99.8 area% (above method)

$^1$H NMR: consistent

K.F. 4.2% microscopy: anisotropic needle-like

EXAMPLE 13

Preparation of the Crystalline Acetate Salt of Amine I

To a mechanically stirred solution of crude amine I free base (5.55 g, 10.0 mmol) in ethanol (50 mL) was added acetic acid (0.60 g, 10.0 mmol). The mixture was seeded (100 mg), and the product allowed to crystallize. The mixture was stirred for 18–24 h at 20°–22° C., filtered, and the cake washed with ethanol (2×5 mL) and acetone (2×5 mL). The product was air-dried to constant weight. Drying the product under vacuum or with heat resulted in the loss of acetic acid.

Yield: 5.11 g (83%) of amine I acetate salt as a white crystalline solid.

HPLC: >99.8 area% (above method)

$^1$H NMR: consistent

K.F. 0.3% microscopy: anisotropic needle-like

EXAMPLE 14

Preparation of the Crystalline Maleate Salt of Amine I

To a mechanically stirred solution of crude amine I free base (5.55 g, 10.0 mmol) in ethanol (50 mL) was added maleic acid (1.16 g, 10.0 mmol). The mixture was seeded (100 mg), and the product allowed to crystallize. The mixture was stirred for 18–24 h at 20:22° C., filtered, and the cake washed with ethanol (2×5 mL) and acetone (2×5 mL). The product was air-dried (2 h), then dried in vacuo (100 mBar, nitrogen sweep, 35° C.) to constant weight.

Yield: 3.02 g (45%) of amine I maleate salt as a white crystalline solid.

HPLC: >99.8 area% (above method)

$^1$H NMR: consistent

K.F. 0.2% microscopy: anisotropic needle-like

EXAMPLE 15

Preparation of the Crystalline Tartrate Salt of Amine I

To a mechanically stirred solution of crude amine I free base (5.55 g, 10.0 mmol) in ethanol (50 mL) was added (+)-tartaric acid 1.50 g and water (400 mg). The mixture was seeded (100 mg), and the product allowed to crystallize. The mixture was stirred for 18–24 h at 20°–22° C., filtered, and the cake washed with ethanol (2×5 mL) and acetone (2×5 mL). The product was air-dried (2 h), then dried in vacuo (100 mBar, nitrogen sweep, 35° C.) to constant weight.

Yield: 6.37 g (86%) of amine I tartrate salt (dihydrate) as a white crystalline solid.

HPLC: >99.8 area% (above method)

$^1$H NMR: consistent

K.F. 4.8% microscopy: anisotropic needle-like

Selected biomedical terms used herein are further defined as follows. The term "preterm labor" shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes.

The term "dysmenorrhea" shall mean painful menstruation.

The term "cesarean delivery" shall mean incision through the abdominal and uterine walls for delivery of a fetus.

The ability of the compounds made by the process of the present invention to antagonize oxytocin makes these compounds useful as pharmacologic agents for mammals, especially for humans, for the treatment and prevention of disorders wherein oxytocin may be involved. Examples of such disorders include preterm labor and especially dysmenorrhea. These compounds may also find usefulness for stoppage of labor preparatory to Cesarean delivery.

Because of the known relationship of vasopressin to oxytocin, the compounds made by the process of the present invention are also useful as vasopressin antagonists. Vasopressin antagonists are useful in the treatment or prevention of disease states involving vasopressin disorders, including their use as diuretics and their use in congestive heart failure. Such compounds have also been implicated in the prevention of enlargement of the prostate organ and can be clinically useful in the treatment if benign prostatic hypertrophy.

The compounds of the method of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a tocolytic agent.

The dosage regimen utilizing such compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drag required to prevent, counter or arrest the progress of the condition.

Oral dosages of such compounds, when used for the indicated effects, will range between about 0.3–6.0 gm/day orally. Intravenously, the most preferred doses will range from 0.1 to about 10 mg/minute during a constant rate infusion. Advantageously, such compounds may be administered in a single daily dose, or the total daily dosage may be administered in divided doses of two, three or four times daily. Furthermore, such compounds can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

Such compounds can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

In addition to the most preferred method of synthesis detailed above, other synthesis schemes are shown below. In Schemes 1 through 8, "$R^1$" through "$R^6$" are as defined in claims 1 and 2 of European Patent EP 0 532 097, published Mar. 17, 1993. In Scheme 2, "R" is defined the same as "$R^{11}$" and "$R^{12}$" in claim 1 of European Patent EP 0 533 240, published Mar. 24, 1993. In Scheme 3, "R" is defined the same as "$R^2$" in claim 5 of EP 0 532 097. In Scheme 4, "$NR_2$" is defined the same as "X" in claim 4 of EP 0 533 240. In Scheme 5, "$R_2$" is defined the same as "$R^{14}$" and "$R^{15}$" in claim 1 of EP 0 532 097. In Scheme 6, "R'" is $C_{1-10}$ alkyl and "R" is defined the same as "$R^2$" in claim 3 of EP 0 532 097. In Scheme 7, "R" is defined the same as "$R^2$" in claim 6 of EP 0 532 097. In Scheme 8, "$R_2$" is defined the same as "$R^{14}$" and "$R^{15}$" in claim 1 of EP 0 532 097.

SCHEME 1

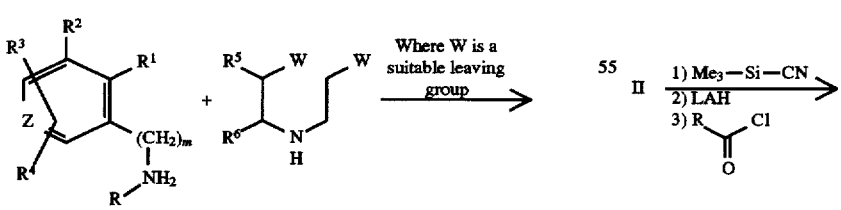

SCHEME 1
-continued

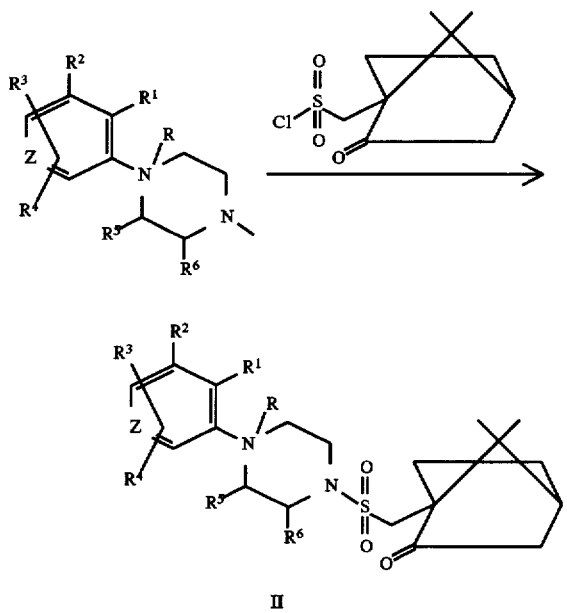

SCHEME 2

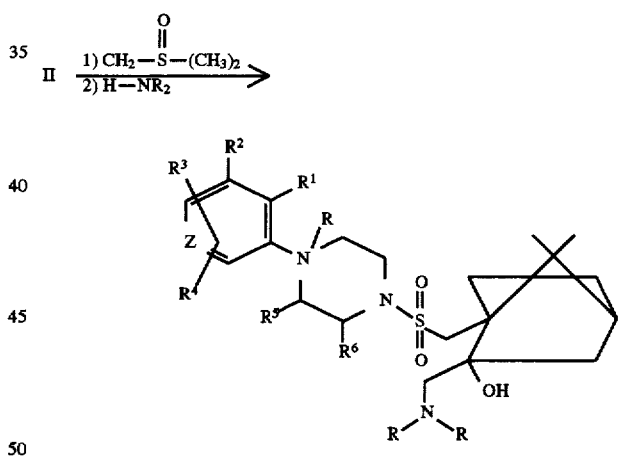

SCHEME 3

SCHEME 3
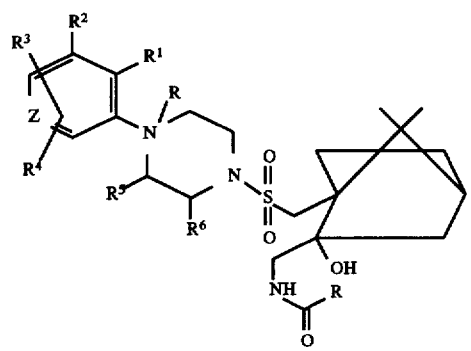
SCHEME 4
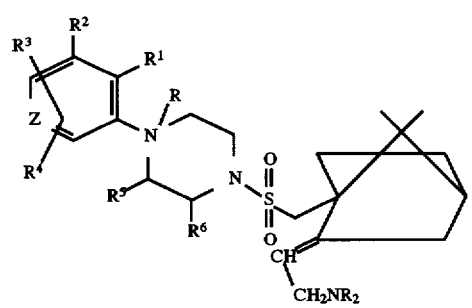
SCHEME 5
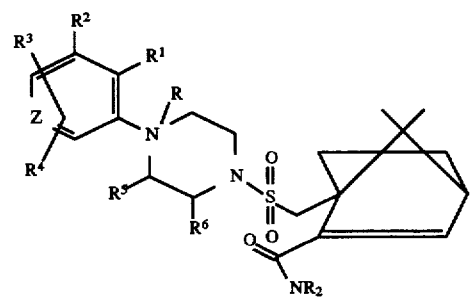
SCHEME 6
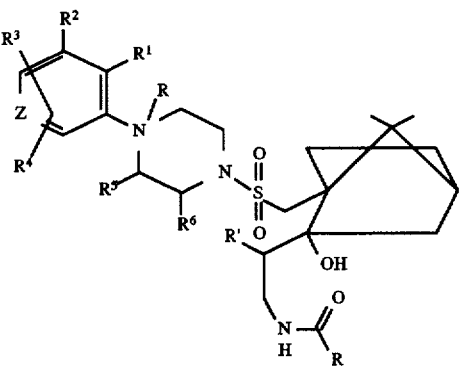
SCHEME 7
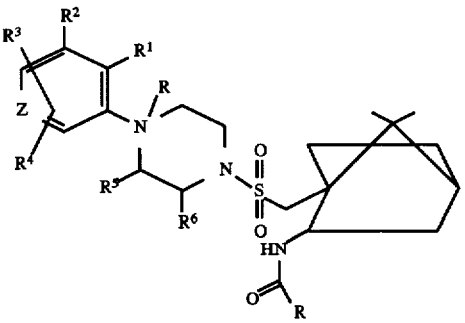
SCHEME 8

-continued
SCHEME 8

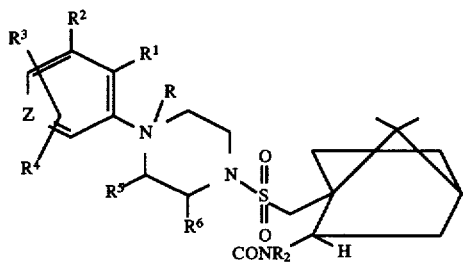

Abbreviations used in the Examples are as follows:
TEA=triethylamine
DIEA=diisopropylethylamine
BOP=benzotriazolyloxytris(dimethylamino) phosphonium hexafluorophosphate
THF=tetrahydrofuran
DMF=dimethylformamide
LAH=lithium aluminum hydride
TFA=trifluoroacetic acid
BOC=t-butyloxycarbonyl

EXAMPLE 8

Radioligand Binding Assays

The high affinity binding of [$^3$H] Oxytocin (OT)([tyrosyl, 3,5-[$^3$H]OT; 30–60 Ci/mmol; New England Nuclear. Boston, Mass.) to uterine OT receptors was based on an assay (Fuchs, A.-R; Fuchs, F.; Soloff, M. S. 1985 J. Clin. Endocrinol. Metab. 60:37) using a crude membrane preparation of uteri taken from diethylstilbestrol dipropionate (DES)-treated (0.3 mg/kg, ip; 18–24) rats. Competition studies were conducted at equilibrium (60 minutes; 22° C.) using 1 nM[$^3$H]OT in the following assay buffer: 50 mM Tris-HCl, 5 mM MgCl$_2$, and 0.1% BSA, pH 7.4. Nonspecific binding (10% of the total binding) was determined using 1 mM unlabeled OT and the binding reaction was terminated by filtration through glass fiber filters using a cell harvester (model 7019, Skatron, Inc., Sterling, Va.). IC$_{50}$ (the concentration of tested compound that inhibits 50% of OT) was reported, unless otherwise noted.

The measurement of [$^3$H]Vasopressin (AVP) ([phenylalanyl-3,4,5-$^3$H]AVP; 80–90 Ci/mmol; New England Nuclear) binding to a crude membrane preparation of male rat liver (AVP-V$_1$ sites) or kidney medulla (AVP-V$_2$ sites) was determined according to the method of Butlen, et al. (Butlen, D.; Guillon, G.; Rajerison, R. M.; Jard, S.; Sawyer, W. H.; Manning, M. 1978 Mol Pharmacol 14:1006).

Competition assays were conducted at equilibrium (30 minutes at 30° C.) using 1 nM [$^3$H]AVP (liver) or 2 nM [$^3$H]AVP (kidney) in the following assay buffer: 100 mM Tris-HCl, 5 mM MgCl$_2$, 0.1% BSA, 50 mM phenylmethylsulfonylfluoride, and 50 mg/ml bacitracin, pH 8.0. Nonspecific binding (5–10% of the total binding) was determined using 10 mM unlabeled AVP, and the binding reaction was terminated by filtration as described above for the [$^3$H]OT binding assay.

K$_i$ values were obtained for each compound from three to six separate determinations of the IC$_{50}$ values (K$_i$=IC$_{50}$/1+ c/K$_d$) (Cheng, Y.-C.; Prusoff, W. H.; 1973 Biochem Pharmacol 22:3099) using K$_d$ values obtained from a saturation binding assay: [$^3$H]OT (uterus), 0.7 nM; [$^3$H]AVP (liver), 0.4 nM; [$^3$H] (kidney), 1.4 nM. Thus, the K$_i$ value for Compound I was found to be 7.7 nM.

While the invention has been described and illustrated with reference to certain preferred embodiments thereof, those skilled in the art will appreciate that various changes, modifications and substitutions can be made therein without departing from the spirit and scope of the invention. It is intended, therefore, that the invention be limited only by the scope of the claims which follow and that such claims be interpreted as broadly as is reasonable.

What is claimed is:

1. A process for the manufacture of a crystalline pharmaceutically acceptable salt of a free base compound of the formula

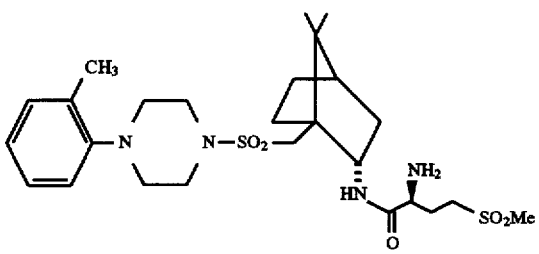

comprising the steps of (a) reacting the compounds of the formulas:

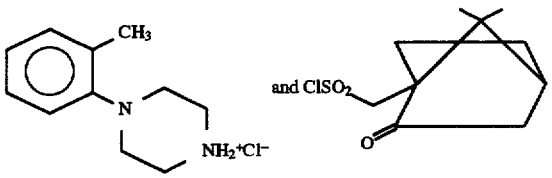

so as to form the ketone of the formula

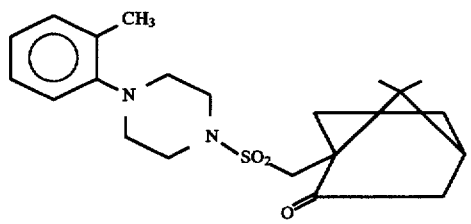

(b) reacting the product of step (a) with hydroxylamine to form the corresponding oxime of the formula

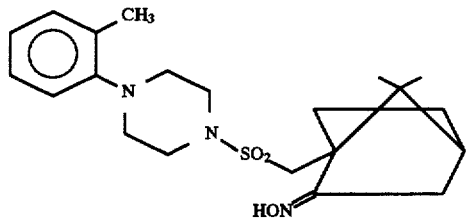

(c) reducing the product of step (b) in the presence of Raney nickel, methanol and a suitable alkali metal hydroxide, alkaline earth hydroxide or ammonium hydroxide to form the exo and endo amine products in a ratio of about 87:13 endo/exo

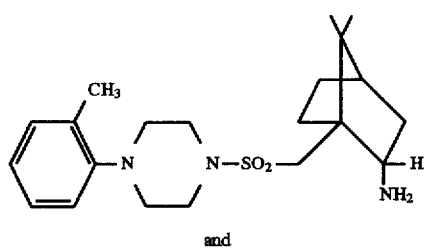

and

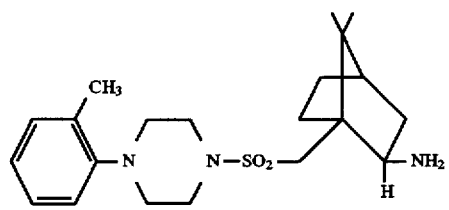

(d) separating the exo and endo amines by selective extraction of the endo amine into aqueous phosphoric acid at pH 4.9±0.1 from the exo amine in toluene (e) selectively reacting the endo amine product of step (c) or (d) in isopropyl acetate in the presence of an acyl activating transfer catalyst and a diimide condensing agent with a compound of the formula

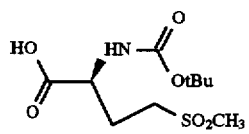

to give the crystalline product of the formula

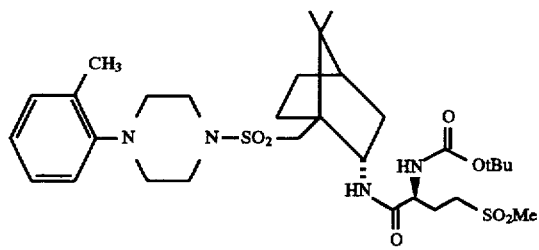

(f) deprotecting the product of step (e) with acid to give the free base product of the formula

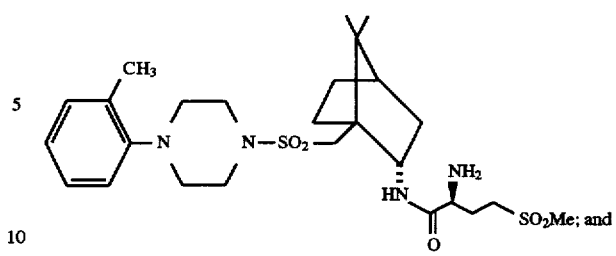

(g) reacting the deprotected free base product of step (f) with a selected acid to give the corresponding crystalline pharmaceutically acceptable acid salt.

2. The process of claim 1, wherein said acid of step (g) is selected from the group consisting of sulfuric acid, hydrochloric acid, phosphoric acid, acetic acid, maleic acid and tartaric acid.

3. The process of claim 2, wherein said acid is sulfuric acid.

4. The process of claim 1, wherein said acyl activating transfer catalyst is hydroxybenzotriazole hydrate.

5. The process of claim 1, where said diimide is ethyl-3-(3-dimethylamino) propyl carbodiimide hydrochloride.

6. The process of claim 1 for the manufacture of a crystalline salt product compound of the formula:

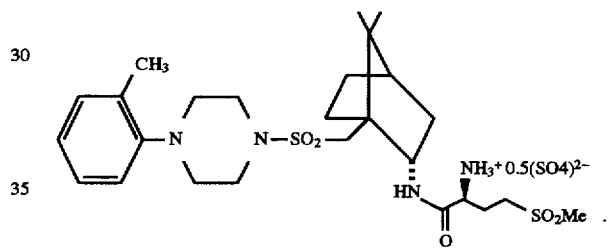

7. A crystalline compound IX of the formula

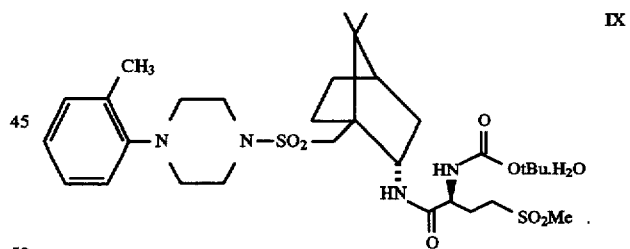

* * * * *